(12) United States Patent
Kurfurst et al.

(10) Patent No.: US 8,597,620 B2
(45) Date of Patent: Dec. 3, 2013

(54) COMPOSITION COMPRISING A TOCOPHEROL PHOSPHATE AND PREPARATION PROCESS

(75) Inventors: Chantal Kurfurst, Saint Jean de Braye (FR); Sabrina Maniguet, Trainou (FR); Jean-Baptiste Grieu, Tokyo (JP); Robin Kurfurst, Saint Jean de Braye (FR); Coralie Robert, Vennecy (FR); Claire Chevalier, Fleury les Aubrais (FR); Sabine Rubio, Fay aux Loges (FR); Takayoshi Sakoda, Kanagawa (JP)

(73) Assignee: LVMH Recherche, Saint Jean de Braye (FR)

( * ) Notice: Subject to any disclaimer, the term of this patent is extended or adjusted under 35 U.S.C. 154(b) by 0 days.

(21) Appl. No.: 13/333,211

(22) Filed: Dec. 21, 2011

(65) Prior Publication Data
US 2012/0171134 A1    Jul. 5, 2012

(30) Foreign Application Priority Data

Dec. 30, 2010  (FR) ...................... 10 61389

(51) Int. Cl.
*A61K 8/67* (2006.01)
*A61K 8/55* (2006.01)
*A61Q 19/02* (2006.01)

(52) U.S. Cl.
USPC ............................ 424/62; 424/401

(58) Field of Classification Search
USPC .................................. 424/401, 62
See application file for complete search history.

(56) References Cited

U.S. PATENT DOCUMENTS 5,858,336 A * 1/1999 Graf et al. ............ 424/65
2006/0257459 A1 11/2006 West et al.

FOREIGN PATENT DOCUMENTS

| EP | 0 798 305 A1 | 10/1997 |
|---|---|---|
| JP | 8 119826 | 5/1996 |
| JP | 11 199424 A | 7/1999 |
| JP | 2008 26617 A | 11/2008 |
| WO | WO 03/011303 A1 | 2/2003 |
| WO | WO2006020164 | * 2/2006 |

OTHER PUBLICATIONS

English Machine Translation of JP11-199424; Accessed Jan. 27, 2013.*
Mintel, Parfums Christian Dior: "Dior Homme Dermo System Anti-Fatigue Firming Eye Serum", Jun. 1, 2009, Datebase accession No. 1121286, XP-000002656557, http://www.gnpd.com.
Senju Seiyaku KK : "JP59044375A" WPI World Patent Information Derwent, vol. 16, No. 84, Mar. 12, 1984 XP002058869.

* cited by examiner

Primary Examiner — Rachael E Bredefeld
(74) Attorney, Agent, or Firm — Hamre, Schumann, Mueller & Larson, P.C.

(57) ABSTRACT

The invention relates to an aqueous solution comprising at least one tocopherol phosphate or one of its salts, at least one non-ionic surface-active agent and at least one diol. The invention also relates to a cosmetic composition advantageously obtained using the said aqueous solution. Finally, it relates to a care method using the said composition.

25 Claims, No Drawings

COMPOSITION COMPRISING A TOCOPHEROL PHOSPHATE AND PREPARATION PROCESS

A subject-matter of the present invention is a novel aqueous solution comprising a tocopherol phosphate, a novel composition for topical application comprising a tocopherol phosphate, a process for the preparation of the said composition and the use of the said composition in the cosmetic and dermatology fields, in particular for depigmenting, lightening or whitening the skin.

STATE OF THE ART

Cosmetic compositions comprising vitamin E or α-tocopherol, as cosmetically or dermatologically active agents, as well as other tocopherol isomers, such as γ-tocopherol and δ-tocopherol, are well known from the state of the art. Generally, in this case, stable derivatives of these tocopherol isomers, such as the esters, in particular the acetate or a phosphate, are used. When a better aqueous solubility is desired, the choice then falls on a polyacid ester, such as phosphate, and more specifically still on a salt of this ester, in particular a sodium salt, although this solubility remains relatively mediocre.

For example, the use of tocopheryl phosphate or one of its salts is known in particular as depigmenting agent, whitening agent or agent having a lightening effect for the skin.

Showa Denko K.K. has filed various patent applications with regard to compositions comprising tocopherol derivatives.

The document WO 2005/102267 describes a composition comprising a tocopherol glycinate in the aqueous phase, in particular in combination with an ascorbic acid derivative. However, the concentration of tocopherol derivative remains low and requires the presence of surfactin, which is a bacterial lipopeptide having very powerful surfactant properties. This document mentions the problem of the low solubility of the tocopherol derivative and indicates that it is necessary to have recourse to the use of a surfactant.

International Application WO 2008/001921 describes antiwrinkle compositions having a suitable stability, which comprise tocopherol phosphate or one of its salts. However, according to the implementational examples, the aqueous phase comprises less than 3% of tocopherol ester.

Application WO 03/094882 describes a whitening or lightening composition for the skin comprising a sodium salt of tocopherol phosphate in the form of an aqueous dispersion or solution having a low concentration of tocopherol.

Application WO 91/11189 of LVMH Recherche also describes cosmetic compositions comprising a disodium salt of tocopherol phosphate. This patent application describes the preparation of a cosmetic composition from a suspension of vesicles formed of this salt.

Thus, the prior art clearly reports this problem of solubility of tocopherol derivatives and their salts in the preparation of cosmetic compositions.

AIMS OF THE INVENTION

There is cause to accurately and reliably assay the amount of tocopherol or one of its derivatives, in particular of the esters, optionally in the salified form, during the preparation of a cosmetic composition. However, this assaying, in order to be sufficiently precise and reliable, must be carried out on a sample in which the tocopherol derivative is completely dissolved. This is because, if a fraction of insoluble tocopherol derivative remained, the assaying would not be sufficiently precise due to the heterogeneity of the preparation at the time of the withdrawal of sample for the assaying.

In the case where a person skilled in the art is not limited by the amount of water which can be used for the preparation of the solution of tocopherol derivative, it is possible to prepare a sufficiently dilute solution which ensures the slow and complete dissolution of this derivative.

However, cases exist in which it is not possible to delete the solution as much as would be desired. This is in particular the case when the water of the final composition is used for the employment of other excipients of the composition, such as, for example, viscosity agents or insoluble fillers.

An excess of water for the preparation of the composition may thus modify the texture of the final composition or its viscosity or also may detrimentally affect the stability thereof.

It is thus desirable, in the case of the tocopherol in the form of a water-soluble derivative, to prepare a sufficiently concentrated solution which makes it possible simultaneously to guarantee precise and reliable assaying of the tocopherol, while allowing a person skilled in the art to prepare a composition which is acceptable from the viewpoint of its stability and of its texture, according to a process which can be operated industrially, regarding in particular the time for the preparation of the tocopherol solution.

It is thus an aim of the present invention to solve the technical problem consisting of the provision of a stable concentrated aqueous solution of tocopherol phosphate or a salt of the latter.

Furthermore, it is an aim of the invention to provide a stable and concentrated aqueous solution of tocopherol phosphate in order to precisely assay the tocopherol phosphate in a cosmetic composition.

Due to the solubility of tocopherol phosphate or of one of its salts, the preparation of a concentrated aqueous solution is problematic and requires the use of at least one solubilizing agent in order to facilitate the dissolution thereof.

The selection of these solubilizing agents is very awkward. This is because the use of one or more solubilizing agents can have an important effect on the final composition to be prepared. In particular, when the compositions are intended to be applied directly to the skin, the texture is very important. In point of fact, solubilizing agents directly impact the texture and can also exhibit undesirable effects for and on the skin, for example by producing an unpleasant sticky effect during the application of the composition.

Thus, in the case of tocopherol phosphate or of one of its salts which is only slightly soluble in water, it is thus a very complex business to obtain a texture which is acceptable to the consumer, that is to say a texture which not only makes possible an easy and uniform application of the composition on the skin but also produces a pleasant feeling during application. This is one of the problems which the invention is targeted at solving.

Another aim of the present invention is to provide a composition for topical application, such as, for example, a cosmetic or dermatological composition.

An aim of the invention is in particular to provide a textured care composition, that is to say a composition with a viscosity and a consistency which make possible an easy and pleasant topical application, comprising tocopherol phosphate or one of its salts. In this composition, the tocopherol phosphate is essentially dissolved: there may remain a tiny fraction, typically less than 10% by weight of the total amount of tocopherol, preferably less than 5% by weight, of undissolved tocopherol and more preferably less than 1% by weight of undissolved tocopherol. Advantageously, all of the tocopherol phosphate present in the composition is in the dissolved form, that is to say in the molecular state, in water or in an aqueous phase present in the composition. The state of dissolution of the tocopherol phosphate can be measured by any method known to a person skilled in the art, such as, for example, high performance liquid chromatography.

Another aim of the present invention is to provide a process for the preparation of a composition for topical application, in particular a cosmetic or dermatological composition, comprising at least one tocopherol phosphate or salt of the latter, the said composition comprising a concentration which can be determined in a reliable and accurate manner.

Another aim of the present invention is to provide a cosmetic care method using such a composition.

Finally, an aim of the present invention is to provide a simple solution to these technical problems which is inexpensive and which can be used on the industrial scale.

SUMMARY OF THE INVENTION

The Applicant company has discovered that it is possible to prepare an aqueous solution comprising a high proportion of tocopherol phosphate or a salt of the latter.

The invention relates in particular to a concentrated aqueous solution of at least one tocopherol phosphate or one of its salts, the said aqueous solution additionally comprising at least one non-ionic surface-active agent and at least one diol.

The invention also relates to a composition for topical application and particularly a cosmetic or dermatological composition, the said composition comprising:
  an aqueous phase,
  at least one tocopherol phosphate or one of its salts,
  at least one polyoxyethylene/polyoxypropylene alkyl ether,
  at least one diol, and
  at least topically acceptable ingredient.

The invention also relates to a method for the preparation of a composition which comprises bringing the aqueous solution of the invention into contact with one or more topically acceptable ingredients and to a care method using the said composition.

The invention thus makes it possible to solve all of the technical problems set out above and in particular to provide a solution and a composition in which tocopherol is completely dissolved and which can be assayed in an accurate and reliable manner. The composition obtained exhibits a texture, a viscosity or a solubility which is acceptable for topical application, in particular for use in cosmetics or in dermatology.

DETAILED DESCRIPTION OF THE INVENTION

A first subject-matter of the present invention is thus an aqueous solution comprising water, at least one tocopherol phosphate or one of its salts, at least one non-ionic surface-active agent and at least one diol.

The aqueous solution is advantageously characterized in that the tocopherol phosphate is dissolved in an amount equal to or greater than 3% by weight, with respect to the weight of the said solution.

Preferably, the aqueous solution comprises from 3 to 25% by weight of tocopherol phosphate or one of its salts and preferably from 5 to 20% by weight, with respect to the total weight of the aqueous solution.

According to a specific embodiment, the aqueous solution consists of water, at least one tocopherol phosphate or one of its salts, at least one non-ionic surface-active agent and at least one diol. It thus comprises solely the components necessary for the tocopherol phosphate or one of its salts to dissolve well.

Preference is given to an alkali metal salt for the tocopherol phosphate and preferably to a sodium salt.

Advantageously, the tocopherol phosphate is α-tocopherol, β-tocopherol, δ-tocopherol or γ-tocopherol phosphate and more particularly sodium γ-tocopherol phosphate.

The non-ionic surface-active agent is preferably chosen from polyoxyethylene/polyoxypropylene alkyl ethers and more preferably from polyoxyethylene/polyoxypropylene tetradecyl ethers.

Such compounds are sold by Nikkol Chemicals under the name of Nikkol PEN.

The preferred compound according to the present invention is POE(20)POP(6) 2-decyltetradecyl ether, sold under the name Nikkol PEN®-4620 (CAS 72484-69-6) and with the INCI name PPG-6-Decyltetradeceth-20.

Preferably, the aqueous solution comprises at least one non-ionic surface-active agent at a total concentration of between 0.5 and 30% by weight and advantageously between 1 and 10% by weight.

Preferably, the diol is advantageously chosen from alkanediols and more particularly from alkanediols comprising from 3 to 8 carbon atoms and more particularly pentane-1,2-diol (also known as pentylene glycol).

Preferably, the aqueous solution comprises at least one diol at a total concentration of between 5 and 60% by weight and more particularly between 7 and 50% by weight.

The invention relates, according to a second aspect, to a composition for topical application and in particular to a cosmetic or dermatological composition, comprising:
  an aqueous phase,
  at least one tocopherol phosphate or one of its salts,
  at least one polyoxyethylene/polyoxypropylene alkyl ether,
  at least one diol and
  at least one topically acceptable excipient.

In this composition, the tocopherol phosphate or one of its salts is advantageously dissolved in water or in the aqueous phase of the composition. The tocopherol is preferably dissolved in a proportion of greater than 90% by weight, preferably of greater than 95% by weight, of the weight of the tocopherol phosphate or one of its salts which was incorporated in the composition. The tocopherol phosphate or one of its salts is advantageously completely dissolved in the water or in the aqueous phase of the composition.

The term "aqueous phase" is understood to mean a phase comprising water and optionally other compounds which are dissolved or dispersed therein.

Preferably, the composition comprises:
  at least 0.1% by weight of the said tocopherol phosphate, advantageously from 0.4 to 8% by weight and more preferably from 0.5 to 6% by weight,
  from 0.05 to 3% by weight of the said polyoxyethylene/polyoxypropylene alkyl ether and more advantageously from 0.1 to 1% by weight,
  from 0.05 to 6% by weight of the said diol and advantageously from 0.1 to 4% by weight.

The composition preferably comprises sodium γ-tocopherol phosphate, at least one polyoxyethylene/polyoxypropylene tetradecyl ether, in particular POE(20)POP(6) 2-decyltetradecyl ether (CAS 72484-69-6), and at least one diol comprising from 3 to 8 carbon atoms, preferably 1,2-pentanediol.

The composition of the present invention is textured, which makes possible, in particular for cosmetic or dermatological compositions, easy and pleasant topical applications around the outline of the eyes and/or over the whole of the face and/or the body and/or over the hands.

The cosmetic composition can be provided in the form of a care product for the skin and advantageously in the form of a serum, of an essence, of a lotion, of an emulsion and in particular of an emulsion of oil-in-water type, of an aqueous gel, of a mask, of a stick or of a patch.

It can also be a skin cleansing product in the form of a cleansing foam or of an abrasive mechanical facial scrub or also a product for making up the complexion in the form of a hydrogel, of an oil-in-water emulsion or of a loose or compact powder, for example obtained by a pasting technique.

According to a first specific embodiment, the composition is a serum or an essence, and is optionally emulsified.

According to another preferred embodiment, the composition is a mask, preferably an emulsified oil-in-water (O/W) mask.

The composition can be more or less fluid and, as the case may be, be packaged in a jar or spray, including pump-action spray, for day or night use.

The composition advantageously comprises at least one topically acceptable excipient.

The composition can in particular comprise one or more water-soluble polymers of synthetic or natural origin, in particular of vegetable origin.

Advantageously, the water-soluble polymers are advantageously chosen from tightening agents capable of forming a film on the skin, so as to obtain a mechanical effect of tautness of the skin ("tightening effect").

The term "tightening agent" is understood to mean a polymer or a blend of polymers, optionally in combination with at least one plasticizing agent, which forms, on the skin, a film which produces the desired mechanical effect (tautness of the skin) while being well tolerated by the user (comfort and absence of tugging).

Preferably, the total amount of water-soluble polymer(s) is between 0.1 and 10% by weight of the composition and preferably between 0.1 and 2% by weight.

In addition, the composition according to the invention can comprise one or more other water-soluble compounds, such as, for example, a $C_6$ or $C_{12}$ sugar or a polyol, advantageously chosen from glucose, sorbitol, sucrose, lactitol, glycerol or one of their ethers or esters or of their derivatives.

These water-soluble molecules are advantageously obtained from a plant extract, it being possible for the said extract to be itself used in the composition.

The composition according to the invention can also comprise one or more other cosmetically acceptable excipients chosen from the group consisting of pigments, dyes, rheology agents, fragrances, sequestering agents, electrolytes, pH adjusters, antioxidants, preservatives, texturing agents, anti-sun agents or sunscreens, or insoluble fillers.

The composition according to the invention can additionally comprise at least one cosmetic or dermatological active agent.

The cosmetic active agent or agents can advantageously be chosen from the group consisting of substances have a depigmenting activity or a lightening activity for the skin; of substances having a slimming activity; of substances having a moisturizing activity; of substances having an anti-inflammatory, calming, soothing or relaxing activity; of substances having an activity in modulating the skin microcirculation in order to improve the radiance of the complexion, in particular of the face; of substances having a sebum-regulating activity for the care of greasy skin; of substances intended to cleanse or purify the skin; of substances having an activity in combating free radicals and/or a protective activity with regard to exposure to the sun, in particular with regard to UV radiation; or of substances having an antiageing activity.

The composition according to the invention can advantageously comprise several cosmetically active substances chosen from the same group or else chosen from groups of substances exhibiting a different cosmetic effect.

The present invention covers in particular depigmenting compositions, whitening compositions or compositions having a lightening effect for the skin, in particular in order to render the colour thereof homogeneous or to reduce the intensity of the colouring of skin pigmentary blemishes and of other cases of lack of homogeneity in pigmentation of the skin.

Such compositions advantageously comprise one or more active agents other than tocopherol phosphate or one of its salts which are chosen from substances having a depigmenting activity or a lightening activity for the skin and keratinous fibres or a whitening activity for the skin and keratinous fibres, such as ascorbyl-2 glucoside (ascorbic acid 2-O-glucoside), an antisense oligonucleotide sequence directed against the messenger RNA encoding tyrosinase or the tyrosinase related-protein 1, azelaic acid, ferulic acid, vitamin $B_3$ or PP, calcium D-pantetheine-S-sulphonate, liquorice or white mulberry extracts, α-lipoic acid, linoleic acid, cation-chelating agents, such as EDTA (ethylenediaminetetraacetic acid), a soy extract, a *Citrus unshiu* extract, diacetyl boldine, retinol, a retinol ester, such as retinol propionate or retinol palmitate, β-ecdysone or tocopherol derivatives other than tocopherol phosphate, such as, for example, potassium ascorbyl tocopheryl phosphate.

A third subject-matter of the invention is targeted at a process for the preparation of a composition for topical application, characterized in that it comprises:

the preparation of a concentrated aqueous solution of tocopherol phosphate, as described above, the mixing of the said concentrated aqueous solution with one or more topically acceptable ingredients, in order to obtain a composition for topical application. All the characteristics which were described above in connection with the description of the composition are applicable to the description of the process of the invention.

According to an alternative form of the invention, the said concentrated aqueous solution of tocopherol phosphate is diluted with water or else mixed or brought into contact with one or more other topically acceptable ingredients dissolved or dispersed in water.

These ingredients are typically one or more active agents and/or one or more excipients which are topically acceptable.

Thus, according to the process of the invention, it is possible to prepare a textured cosmetic composition which is stable over time and which has a concentration of tocopherol phosphate which is very accurately assayed.

Finally, the preparation process of the invention can be carried out on the industrial scale, as a result of the rapid and complete dissolution of the tocopherol phosphate or of one of its salts, using the system of solubilizing agents described above.

The invention also relates to a cosmetic composition capable of being obtained from the process described above.

The invention also relates to a cosmetic composition capable of being obtained from an aqueous solution, in particular by dilution, in water or in an aqueous phase, of this aqueous solution, which comprises water, at least one tocopherol phosphate or one of its salts, at least one non-ionic surface-active agent and at least one diol, in which the tocopherol phosphate is dissolved in an amount equal to or greater than 3% by weight, with respect to the total weight of the aqueous solution.

According to a final aspect, the invention is also targeted at the use, on a concerned area of the body, of an effective amount of a cosmetic composition as defined above or in the following description, in order to obtain the desired cosmetic or dermatological effect.

According to a first alternative form, the present invention is targeted at the use of a composition according to the invention to depigment, whiten or lighten the skin, in particular in order to unify the complexion thereof or to reduce the intensity of the colouring of skin pigmentary blemishes and of other cases of lack of homogeneity in pigmentation of the skin.

The said use more particularly comprises the application, to at least one hyperpigmented area of the skin or keratinous fibres, of the body or of the face, of an effective amount of at least one cosmetic or dermatological composition as defined above, in order:

- to prevent or tone down skin pigmentary blemishes (areas of hyperpigmentation) or the colouring of hyperpigmented areas of the skin, in particular those consisting of various skin dyschromias, in particular resulting from contact dermatitis, drug-induced photodermatitis, melasma, senile lentigo (liver spots) or solar lentigo, pigmentary blemishes resulting from impacts, scars, burns or acne lesions, or pigmentary blemishes brought about by allergic or phototoxic reactions;
- to prevent or tone down pigmentation of the periphery of depigmented areas of skin, resulting in particular from leucodermas, such as vitiligo;
- to improve the homogeneity of the colouring of the skin or to lighten the complexion thereof.

According to another alternative form, the invention relates to the use of the composition as defined above in an amount effective in preventing or delaying the appearance of signs of ageing of the skin or in slowing down the effects thereof, in particular intended to tone up the skin, and/or to promote the toning down or the resorption of wrinkles, commonly known as antiageing effect, or to protect the skin from oxidative stress and stress brought about by exposure to the sun.

The composition is then more particularly applied to the face, the outline of the eyes, the hands, the neck and/or the neckline.

The various embodiments of the present invention are described alone and in their diverse combinations. Thus, the various embodiments or alternative forms are not limited to one aspect of the invention but concern all the aspects of the invention.

A person skilled in the art also understands that the invention thus defined solves the technical problem set out above in a satisfactory, reliable and inexpensive way which can be used on the industrial and cosmetic scale.

Other aims, characteristics and advantages of the invention will become clearly apparent in the light of the explanatory description which will follow, made with reference to several implementational examples and tests carried out in vitro and in vivo which follow, given simply by way of illustration and which cannot in any way limit the scope of the invention.

For the description and in particular in the examples, the percentages are given by weight; the temperature is ambient temperature, i.e. 22° C. plus or minus 3° C.; the pressure is atmospheric pressure, unless otherwise indicated.

IMPLEMENTATIONAL EXAMPLES ACCORDING TO THE INVENTION

The examples below exhibit uses of the invention.

Example 1 illustrates the concentrated aqueous solution of tocopherol phosphate of the invention, which is subsequently used in Examples 2 to 5 for the preparation of textured cosmetic compositions, that is to say with a viscosity and a consistency which make possible an easy and pleasant topical application.

The compositions of Examples 2 to 5 are characterized by the preparation of aqueous phases requiring a minimum amount of water for dissolving, dispersing and more generally employing certain compounds of their formulations. This is the case in particular of aqueous phases comprising inorganic or organic fillers (Ex. 2), gelling polymers (Ex. 3, 4 and 5) or cosmetic agents (Ex. 4 and 5). However, in order to retain its texture and its viscosity, the final composition may not comprise more than a certain proportion of water, which limits the amount of water which can be used to completely dissolve the tocopherol phosphate before it is incorporated in the final composition.

Thus it is then necessary to find an acceptable balance in the distribution of the water between the various aqueous phases employed, between the water necessary for the use of the compounds of the formulation and the water necessary to dissolve the tocopherol phosphate.

It is in this respect that the concentrated aqueous solution of tocopherol phosphate of the invention exhibits an unexpected and particularly useful advantage in so far as it makes it possible to solve this problem of distribution of water between the various aqueous phases of the formulation of each composition of the examples and more generally for the preparation of the compositions of the invention.

Use of such a concentrated aqueous solution thus makes it possible to simultaneously obtain the complete dissolution of the tocopherol phosphate salt and a texture satisfactory for application of the compositions to the skin.

Method for the Assaying of Tocopherol Phosphate by HPLC

The concentrated solution of γ-TPNa obtained in Example 1 and the compositions prepared in Examples 2 to 5 are assayed for tocopherol phosphate by HPLC according to the following conditions:

Column: C18, 125 mm×4 mm×5 μm
Elution gradient:—Eluent A: sodium acetate/acetic acid buffer pH 4.2
Eluent B=methanol/THF (80/20)
Flow rate: 1 ml/min
Analytical time: 20 min.
Detection: UV at 290 nm
Preparation of the Solutions
Diluent: Eluent A/eluent B (20/80 v/v)
Standard solution for the calibration=solution of γ-TPNa at 0.08 mg/ml of diluent.
Solution for the assaying of the concentrated solution (Ex. 1):
100 mg of the concentrated aqueous solution are withdrawn and diluted in 100 ml of diluent.
Solution for the assaying of the compositions (Ex. 2 to 5):
200 mg of the composition are withdrawn and dispersed/diluted in 20 ml of diluent.

Example 1

Preparation of the Concentrated Solution of The Invention Comprising the Sodium Salt of γ-Tocopherol Phosphate A concentrated solution of a tocopherol phosphate salt is prepared by choosing PPG-6-Decyltetradeceth-20 (Nikko)

PEN®-4620) as polyoxyethylene/polyoxypropylene alkyl ether and 1,2-pentanediol as diol.

The concentrated solution of the invention exhibits the following formulation:

| Designations | % by weight |
|---|---|
| PPG-6-Decyltetradeceth-20 (Nikkol PEN ®-4620) | 3.5 |
| 1,2-Pentanediol | 17.4 |
| Sodium salt of γ-tocopherol phosphate (γ-TPNa) | 8.7 |
| Purified water | q.s. for 100 |

Preparation Process

The Nikkol PEN®-4620 is heated to 40° C. and is successively treated with the water and then the 1,2-pentanediol. The phase obtained is stirred using a deflocculator at 700 revolution/minute until dissolution is complete.

The γ-TPNa is added to the preceding phase with stirring at 700 revolution/min and is then left standing for 1 h.

The phase obtained is clear to the naked eye.

Result of the Assaying of the γ-TPNa in the Concentrated Solution Prepared Above: 8.7% by Weight.

This result confirms the complete dissolution of the γ-TPNa in the concentrated solution of the example, since the amount added at the start is reencountered in its entirety by assaying the concentrated solution. This complete dissolution of the γ-TPNa in a reduced volume of water ensures the accuracy of the assaying of γ-TPNa in the compositions prepared using the concentrated solution, including those presented in the following Examples 2 to 5.

Example 2

Lightening Purifying Mask

The composition is a mask having 1% by weight of γ-TPNa which comprises fillers (kaolin and titanium dioxide) requiring the use of a significant amount of water in order to disperse this filler in the aqueous phase of the composition.

The water included in phases B and C is no longer available to dissolve the γ-TPNa. It is thus necessary to prepare a phase highly concentrated in γ-TPNa using a limited amount of water, while making sure that the γ-TPNa is indeed completely dissolved in the said concentrated solution.

The Mask Exhibits the Following Composition:

| Deignations | % by weight | Phase |
|---|---|---|
| Jojoba esters | 3 | A |
| Ethylhexyl palmitate | 8.8 | A |
| Steareth-21 | 1.6 | A |
| $C_{16}$-$C_{18}$ Fatty alcohols | 2.8 | A |
| O/W Emulsifier (HLB 12) | 3.2 | A |
| Phenoxyethanol | 0.7 | B |
| Vegetable glycerol | 3.0 | B |
| Butylene glycol | 3.0 | B |
| Exfoliating agent | 1.1 | B |
| Xanthan gum | 0.2 | B |
| Purified water | q.s. for 100 | B |
| Kaolin | 17 | C |
| Titanium dioxide | 5.0 | C |
| Purified water | 17 | C |

-continued

| Designations | % by weight | Phase |
|---|---|---|
| Concentrated solution of γ-TPNa according to Ex. 1 | 11.5 | D |
| Sepigel ® 305 | 1 | E |
| Tromethamine | 0.84 | E |
| Purified water | 0.3 | E |
| Fragrance | 2.54 | E |

Sepigel ® 305: Polyacrylamide/C13-14/Isoparaffin/Laureth-7 water

Preparation Process

Phase A is heated at 70° C. until completely molten. Phase B is heated separately at 70° C. with stirring corresponding to 50% of the maximum stirring speed of the Ystral device (Le Chesnay, France).

Phase A is emulsified under hot conditions (70° C.) in phase B with Ystral stirring at 60% of the maximum stirring speed of the device, to form an oil-in-water (O/W) emulsion.

The compounds of phase C are dispersed in water with stirring, which phase C is subsequently added under hot conditions (50° C.) to the aqueous phase of the O/W emulsion obtained above with Ystral stirring at 50% of the maximum stirring speed of the device.

Phase D is added at 40° C. to the O/W emulsion obtained above.

The compounds of phase E are added A one by one at 35° C. with Ystral stirring at 50% of its power.

The composition is thick and is packaged in a jar.

The composition is applied to the face and then retained for a time sufficient to obtain the desired effect.

Example 3

Whitening Day Cream

The day cream is an O/W emulsion comprising an aqueous phase in the form of a gel. The preparation of the gel requires a sufficient amount of water, so as to ensure that the gel is homogeneous and has a viscosity acceptable for this type of formulation.

The concentrated solution of γ-TPNa of the invention is used to manufacture the composition, the complete dissolution of the γ-TPNa in the final composition being assured.

| Designations | % by weight | Phase |
|---|---|---|
| Phenoxyethanol | 0.7 | A |
| Acrylates/C10-30 Alkyl Acrylate Crosspolymer | 0.3 | A |
| Purified water | q.s. for 100 | A |
| 95% Cetyl alcohol | 2 | B |
| Shea butter | 4 | B |
| Jojoba esters | 4 | B |
| Sweet almond oil | 2 | B |
| Dimethicone | 2 | B |
| Sepigel ® 305 | 4 | C |
| Sodium Hydroxide | 0.08 | D |
| Purified water | 0.7 | D |
| Concentrated solution of γ-TPNa according to Ex. 1 | 11.5 | E |
| Fragrance | 0.2 | F |
| Glycerol | 5 | F |
| Butylene glycol | 4.6 | F |
| Water-soluble lightening active agent | 0.4 | F |

Sepigel ® 305: Polyacrylamide/C13-14/Isoparaffin/Laureth-7 water

Preparation Process:

The compounds of phase A are dispersed in water at ambient temperature with fairly vigorous stirring (Staro mixer (Montrouge, France)) until the mixture is completely homogenous.

Phases A and B are heated separately to 75° C.

Phase B is slowly emulsified in phase A (O/W emulsion) with fairly vigorous Staro stirring and then the mixture is allowed to cool under steady stirring.

Phase C is added to the aqueous phase of the emulsion at 50° C. Cooling is continued while maintaining the stirring in order to homogenize the emulsion.

The prepared phases D and then E (comprising the γ-TPNa) are added at 40° C. Finally, the ingredients of phase F are added one by one.

The composition comprising 1% by weight of γ-TPNa is packaged in a jar.

The composition is applied to the skin each morning in order to obtain a lightening effect on the skin.

Example 4

Lightening Emulsified Essence

The composition comprises polymeric gelling agents which require the use of water in order to form a homogeneous gel having an acceptable viscosity.

Furthermore, a large amount of water is necessary in order to dissolve or disperse the active agents (phase G) in the composition.

The water used to this end is no longer available to dissolve the γ-TPNa. It is necessary to prepare a phase highly concentrated in γ-TPNa using a limited amount of water, while making sure that the γ-TPNa is indeed completely dissolved in the said concentrated solution.

The composition exhibits the following formulation:

| Designations | % by weight | Phase |
|---|---|---|
| Anionic polysaccharides | 0.07 | A |
| Butylene glycol | 4.1 | A1 |
| Phenoxyethanol | 0.73 | A1 |
| Purified water | 32.7 | A1 |
| Exfoliating agent | 1.1 | A2 |
| Aminomethyl propanediol | 0.6 | A2 |
| Biosaccharide gum-1 | 0.03 | A2 |
| Maltitol | 1 | A2 |
| Polyethylene glycols | 1.4 | A2 |
| Purified water | q.s. for 100 | A2 |
| Acrylates/C10-30 Alkyl Acrylate Crosspolymer | 0.6 | A3 |
| Xanthan gum | 0.07 | A3 |
| PEG-60 hydrogenated castor oil | 1.0 | B |
| Caprylic/capric/succinic triglyceride | 3.5 | B |
| Isohexadecane | 1 | B |
| Fragrance | 0.2 | B |
| PEG-7 glyceryl cocoate | 0.4 | B |
| Lecithins | 0.1 | B |
| Concentrated solution of γ-TPNa according to Ex. 1 | 11.5 | C |
| Purified water | 5.0 | D |
| Sodium hydroxide | 0.3 | D |
| 96.2% v/v Ethanol | 3 | E |
| Butylene glycol | 3 | F |
| Vegetable glycerol | 4 | F |
| Polymethylsilsesquioxane | 1.5 | F |
| Active agents (antiageing and moisturizing active agents) | 0.2 | G |
| Purified water | 14 | G |
| 96.2% v/v Ethanol | 1.0 | G |
| Phenoxyethanol | 0.2 | G |
| Glycols | 0.9 | G |

Preparation Process

Phase A1 is prepared under hot conditions (80-85° C.) in a water bath with 50% Ystral stirring until a smooth aqueous gel is obtained.

The mixture is allowed to cool to 40° C. and then the compounds of phase A2 are added with Ystral stirring at 70% of the maximum stirring speed of the device, before allowing the phase obtained to swell for 1 hour 30 minutes.

The compounds of phase A3 are added with vigorous stirring (Ystral at 80% of the maximum stirring speed of the device).

The gelled phase B is prepared at 45° C. with Ystral stirring at 60% of the maximum stirring speed of the device.

Once the two phases have cooled to ambient temperature, phase B is emulsified in phase A to form an oil-in-water (O/W) emulsion.

Phase C is prepared according to Example 1. It is added at ambient temperature to the O/W emulsion prepared above.

Phase D is added at ambient temperature to the emulsion obtained above.

Phases E, F and G are prepared separately at 40° C. and then cooled. They are successively added to the composition at ambient temperature.

After addition of the final phase, stirring is carried out at least for 10 minutes until a homogeneous emulsion is obtained.

The composition having 1% by weight of γ-TPNa is a lightening emulsified essence packaged in a pump-action spray.

The composition is applied in the morning and/or in the evening to the face or a part of the face.

Example 5

Lightening Essence

Like Example 4, the composition comprises polymeric gelling agents and active agents which require the use of a large amount of water for their use in the composition of the following example.

As explained above, it is necessary to prepare a phase highly concentrated in γ-TPNa using a limited amount of water, while making sure that the γ-TPNa is indeed completely dissolved in the said concentrated solution.

The formulation of the composition is as follows:

| Designations | % | Phase |
|---|---|---|
| Aminomethyl propanediol | 0.4 | A |
| Biosaccharide gum-1 | 0.02 | A |
| Butylene glycol | 4.2 | A |
| Acrylates/C10-30 Alkyl Acrylate Crosspolymer | 0.4 | A |
| Na$_2$EDTA•2H$_2$O | 0.2 | A |
| Glycerol | 7.0 | A |
| Xanthan gum | 0.07 | A |
| Maltitol | 1.0 | A |
| Phenoxyethanol | 0.8 | A |
| Sodium phosphate | 0.03 | A |
| Disodium phosphate | 0.03 | A |
| Anionic polysaccharides | 0.05 | A |
| Purified water | q.s. for 100 | A |
| Caprylyl methicone | 1.5 | B |
| Dimethicone | 1.5 | B |
| Concentrated solution of γ-TPNa according to Ex. 1 | 23 | C |
| Polymethylsilsesquioxane | 2.0 | D |
| 96.2% v/v Ethanol | 2.1 | E |
| PEG-7 glyceryl cocoate | 0.2 | E |
| Active agents (antiageing and moisturizing agents) | 0.1 | F |
| Glycerol | 0.4 | F |
| Purified water | 7.2 | F |

Preparation Process

Phase A is prepared under hot conditions (80° C.) using a deflocculator until a smooth and homogeneous aqueous gel is obtained.

The prepared phase B is slowly added to phase A.

Phase C is prepared in accordance with Example 1 and is then added to the composition obtained above.

Phases D, E and F, prepared at the time of use, are added.

The composition having 2% by weight of γ-TPNa is an essence intended to lighten the skin. Its fluid texture makes possible packaging in a pump-action spray.

The composition is applied in the morning and/or in the evening to the face or a part of the face.

The compositions obtained according to the above examples exhibit a texture, a viscosity or a stability acceptable for topical application, in particular for use in cosmetics or in dermatology.

The invention claimed is:

1. An aqueous solution, consisting of:
water,
at least one γ-tocopherol phosphate salt,
at least one non-ionic surface-active agent, and
at least one diol,
wherein the γ-tocopherol phosphate salt is completely dissolved in the aqueous solution, and
wherein the γ-tocopherol phosphate is present in an amount from 5% to 20% by weight, with respect to the total weight of the aqueous solution.

2. The aqueous solution according to claim 1, wherein the γ-tocopherol phosphate salt is an alkali metal salt.

3. The aqueous solution according to claim 1, wherein the non-ionic surface-active agent is a polyoxyethylene-polyoxypropylene alkyl ether.

4. The aqueous solution according to claim 1, wherein the non-ionic surface-active agent is POE(20)POP(6) 2-decyltetradecyl ether.

5. The aqueous solution according to claim 1, wherein the at least one non-ionic surface-active agent is present in an amount of between 0.5 and 30% by weight.

6. The aqueous solution according to claim 1, wherein the diol is alkanediol comprising from 3 to 8 carbon atoms.

7. The aqueous solution according to claim 1, wherein the at least one diol is present in an amount of between 5 and 60% by weight.

8. A composition for topical application, comprising:
the aqueous solution according to claim 1, wherein the γ-tocopherol phosphate salt is sodium γ-tocopherol phosphate, wherein the non-ionic surface-active agent is POE(20)POP(6) 2-decyltetradecyl ether and wherein the diol is 1,2-pentanediol.

9. The composition according to claim 8, wherein the aqueous solution consists of
from 0.4 to 8% by weight of the γ-tocopherol phosphate salt,
from 0.05 to 3% by weight of the non-ionic surface active agent, and
from 0.05 to 6% by weight of the diol.

10. The composition according to claim 8, wherein in the aqueous phase and wherein the composition is provided in the form of: a care product for the skin, a serum, an essence, a lotion, an emulsion, an aqueous gel, a mask, a stick, a patch, a cleansing product for the skin, a product for making up the complexion, or a loose or compact powder.

11. The composition according to claim 8, wherein the composition comprises topically acceptable excipient.

12. The composition according to claim 8, further comprising a substance having (1) a depigmenting activity or a lightening activity for the skin and keratinous fibres or (2) a whitening activity for the skin and keratinous fibres.

13. The composition of claim 10, wherein the emulsion is an oil-in-water emulsion.

14. The composition of claim 10, wherein the cleansing product for the skin is in the form of a cleansing foam or an abrasive mechanical facial scrub.

15. The composition of claim 12, wherein the substance is at least one selected from the group consisting of ascorbyl-2 glucoside (ascorbic acid 2-O-glucoside), an antisense oligonucleotide sequence directed against a messenger RNA encoding tyrosinase or a tyrosinase related-protein 1, azelaic acid, ferulic acid, vitamin $B_3$, calcium D-pantetheine-S-sulphonate, a liquorice extract, a white mulberry extract, α-lipoic acid, linoleic acid, a cation-chelating agent, a soy extract, a *Citrus unshiu* extract, diacetyl boldine, retinol, a retinol ester, β-ecdysone and a tocopherol derivative other than tocopherol phosphate.

16. The composition of claim 15, wherein the cation-chelating agent is EDTA (ethylenediaminetetraacetic acid).

17. The composition of claim 15, wherein the retinol ester is at least one selected from the group consisting of retinol propionate and retinol palmitate.

18. The composition of claim 15, wherein the tocopherol derivative other than tocopherol phosphate is potassium ascorbyl tocopheryl phosphate.

19. A method for preparing a composition, comprising:
mixing the aqueous solution of claim 1 with a topically acceptable ingredient, wherein the γ-tocopherol phosphate salt is sodium γ-tocopherol phosphate, wherein the non-ionic surface-active agent is POE(20)POP(6) 2-decyltetradecyl ether and wherein the diol is 1,2-pentanediol in the aqueous solution.

20. The method of claim 19, wherein the at least one non-ionic surface-active agent is present in the aqueous solution in an amount of between 0.5 and 30% by weight.

21. The method of claim 19, wherein the at least one diol is present in the aqueous solution in an amount of between 5 and 60% by weight.

22. The method of claim 21, wherein the at least one diol is present in the aqueous solution in an amount of between 7 to 50% by weight.

23. A method, comprising: applying an effective amount of a composition according to claim 8 on a concerned area of the body to depigment, whiten or lighten the skin, in order to unify the complexion thereof or to reduce the intensity of the colouring of skin pigmentary blemishes.

24. A method, comprising: applying an effective amount of a composition according to claim 8 on at least one hyperpigmented area of the skin or of the keratinous fibres, of the body or of the face, in order:
to tone down skin pigmentary blemishes or the colouring of hyperpigmented areas of the skin;
to tone down pigmentation of the periphery of depigmented areas of skin, resulting from leucodermas.

25. A method, comprising: applying an effective amount of a composition according to claim 8 on a concerned area of the body to delay the appearance of signs of ageing of the skin or to slow down the effects thereof.

* * * * *